(12) United States Patent
Hansen et al.

(10) Patent No.: US 9,433,589 B2
(45) Date of Patent: Sep. 6, 2016

(54) INJECTABLE PHARMACEUTICAL COMPOSITIONS COMPRISING ADRENALINE AND CITRIC ACID

(71) Applicant: Rigshospitalet, Kobenhavn O (DK)

(72) Inventors: Philip Hansen, Holte (DK); Pär Johansson, Dösjebro (SE); Jens Kindtler, Hørsholm (DK)

(73) Assignee: Rigshospitalet, Kobenhavn Ø (DK)

( * ) Notice: Subject to any disclaimer, the term of this patent is extended or adjusted under 35 U.S.C. 154(b) by 0 days.

(21) Appl. No.: 14/898,573

(22) PCT Filed: Jun. 17, 2014

(86) PCT No.: PCT/DK2014/050171
§ 371 (c)(1),
(2) Date: Dec. 15, 2015

(87) PCT Pub. No.: WO2014/202088
PCT Pub. Date: Dec. 24, 2014

(65) Prior Publication Data
US 2016/0113891 A1    Apr. 28, 2016

(30) Foreign Application Priority Data
Jun. 17, 2013 (DK) .................. 2013 70322

(51) Int. Cl.
| | | |
|---|---|---|
| *A61K 31/135* | (2006.01) | |
| *A61K 31/137* | (2006.01) | |
| *A61K 9/00* | (2006.01) | |
| *A61K 47/12* | (2006.01) | |
| *A61K 31/194* | (2006.01) | |
| *A61K 47/02* | (2006.01) | |
| *A61K 47/18* | (2006.01) | |
| *A61K 47/22* | (2006.01) | |

(52) U.S. Cl.
CPC ........... *A61K 31/137* (2013.01); *A61K 9/0019* (2013.01); *A61K 31/194* (2013.01); *A61K 47/02* (2013.01); *A61K 47/12* (2013.01); *A61K 47/183* (2013.01); *A61K 47/22* (2013.01)

(58) Field of Classification Search
CPC ..................................... A61K 31/135
USPC ......................................... 514/649
See application file for complete search history.

(56) References Cited

U.S. PATENT DOCUMENTS

2008/0269347 A1   10/2008   Bruss et al.
2012/0029085 A1    2/2012   MacKay

FOREIGN PATENT DOCUMENTS

EP    0858803 A1    8/1998
FR    2779061 A1    12/1999

OTHER PUBLICATIONS

International Search Report and Written Opinion issued in co-pending international application No. PCT/DK2014/050171, mailed Sep. 1, 2014.

*Primary Examiner* — Raymond Henley, III
(74) *Attorney, Agent, or Firm* — Dinsmore & Shohl LLP; Weston R. Gould

(57) ABSTRACT

The present invention relates to injectable pharmaceutical compositions showing improved storage stability said compositions comprising adrenaline and citric acid showing improved storage stability.

17 Claims, No Drawings

INJECTABLE PHARMACEUTICAL COMPOSITIONS COMPRISING ADRENALINE AND CITRIC ACID

FIELD OF INVENTION

The present invention relates to injectable pharmaceutical compositions showing improved storage stability. In particular, the present invention relates to compositions comprising adrenaline and citric acid.

BACKGROUND OF INVENTION

Adrenaline (also known as epinephrine) is a hormone and a neurotransmitter. Adrenaline has many functions in the body, such as regulating heart rate, blood pressure and air passage diameters, and metabolic shifts, such as energy metabolism. Release of adrenaline is a crucial component of the fight-or-flight response of the sympathetic nervous system.

Adrenaline, (−)-3,4-dihydroxy-[(methylamino)methyl] benzyl alcohol, is a member of a group of monoamines called the catecholamines. It is produced in some neurons of the central nervous system, and in the chromaffin cells of the adrenal medulla from the amino acids phenylalanine and tyrosine.

Adrenaline is available in a variety of formulations suited for different clinical indications and routes of administration, for example by injection, by inhalation, or by topical use. Its uses include combating low blood pressure during hemorrhagic or allergic shock; opening the airways during asthmatic attack; restricting the distribution of locally administered drugs such as local anesthetics; reducing nasal congestion; and/or performance aid in emergency situations. The hydrochloride, sulphate, and bitartrate salts are known to be used in pharmaceutical compositions.

Adrenaline may also be used to stimulate or improve the coagulation competence in a subject to control bleeding disorders that have several causes such as clotting factor deficiencies (e.g. hemophilia A and B or deficiency of coagulation Factors XI or VII) or clotting factor inhibitors and also to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease.

Bleeding is also a major problem in connection with surgery and other forms of tissue damage.

Adrenaline oxidizes easily and darkens slowly on exposure to air and therefore instability of current adrenaline formulations constitute a major problem during storage if this issue is not properly addressed.

Today, dilute solutions are partially stabilized by the addition of chlorobutanol and by reducing agents, such as sodium bisulfite or ascorbic acid. Unfortunately, allergic reactions to the bisulfite preservatives are often observed, such that formulations containing bisulfites will be contraindicated in individuals having such allergies. Adrenaline contains an amine group and therefore it forms salts with acids including the hydrochloride, the borate, and the bitartrate. The bitartrate has the advantage of being less acidic and is used in the eye because its solutions have a pH close to that of lacrimal fluid. Adrenaline is destroyed readily in alkaline solutions by aldehydes, weak oxidizing agents and oxygen of the air. Other disadvantages of adrenaline include a short duration of action, decomposition of its salts in solution, vasoconstriction action frequently followed by vasodilation and inactivity on oral administration.

Instability has also been observed when drugs are combined with adrenaline. For example, when lidocaine hydrochloride is mixed with adrenaline hydrochloride the buffering capacity of the lidocaine raises the pH of the intravenous admixtures above 5.5, the maximum necessary for stability of the adrenaline, to about 6. Under these conditions, the adrenaline hydrochloride will begin to deteriorate within several hours.

US patent application no. US 2008/0269347 describes an epinephrine formulation that has enhanced stability. In particular the formulations disclosed in this document are injectable formulations. The formulations comprise epinephrine, EDTA and one or more antioxidant such as cysteine, citric acid, acetylcystein or thioglycerol. The formulations are suitable for any medical condition that is in need of epinephrine, such as anaphylaxis, asthma or cardiac arrest. The formulations disclosed in this document comprises about 1 mg/ml epinephrine.

US patent application no. US 2012/0029085 also relates to stabilization of compositions, which contain catecholamine drugs, such as for example epinephrine.

The stability of these compositions is achieved through the inclusion of an appropriately selected pH buffer and a thiol agent, based on redox and pH buffering principles including pKa of the buffer and of the reversibly protonated amine group. In this document the stabilized pharmaceutical injection solutions comprise 1 mg/ml epinephrine.

Pharmaceutical compositions on the market today typically contain a high concentration of adrenaline in order to fulfil the requirements with regard to stability. These compositions must be diluted before they can be administered to the subject in need thereof. The consequence for not using diluted compositions may be detrimental, and the subject's life may be lost. In case of emergencies valuable time may be wasted performing this act of dilution. Moreover, the dilution act may induce a risk of contamination, especially if the medicament must be administered in the field, such as for example at a car crash.

Clearly there remains a need to develop pharmaceutical injection solutions that are prepared and stored as ready for use medicaments and which fulfils the requirements with regard to stability during periods of storage.

SUMMARY OF INVENTION

The present invention relates to injectable pharmaceutical compositions showing improved storage stability said compositions comprising adrenaline and citric acid.

The present invention is concerned with novel ready-to-use solutions comprising a very low concentration of adrenaline and at the same time having enhanced stability, which makes these solutions a superior choice to store in emergency places such as for example pharmacies, hospitals and in mobile or emergency medical aid kits.

In particular the present invention is directed to a pharmaceutical composition comprising low concentrations of adrenaline and citric acid. In certain embodiments the composition does not comprise lidocaine and/or an amino acid.

The present invention also relates to the use of the injectable pharmaceutical composition in the treatment of an adrenaline-requiring condition such as for example coagulation disorder, bleeding, excessive bleeding, and/or bleeding caused by tissue damage or surgical procedure.

DETAILED DESCRIPTION OF THE INVENTION

The present invention solves the problem of providing an injectable pharmaceutical composition comprising adrenaline, which can be stored as a ready to use formulation.

The inventors of the present invention have surprisingly found that an injectable pharmaceutical composition, which is stable for several months, can be obtained by the formulation comprising:

(a) 0.2-50 µg/ml adrenaline, and
(b) citric acid.

In some embodiments the composition comprises
(a) 0.2-50 µg/ml adrenaline, and
(b) citric acid,
with the proviso that the composition does not comprise lidocaine and/or an amino acid.

In other embodiments the composition comprises
(a) 0.2-4 µg/ml adrenaline, and
(b) citric acid.

It has been found that such formulations are stable for at least 6 months during storage.

The compositions of the present invention differ from the commercial products, which are on the market today, because the commercial products comprise both adrenaline and Na-metabisulfite as a preservative or antioxidant at much higher concentration levels. Both the higher concentration of adrenaline and the presence of Na-metabisulfite are meant to be necessary in order for the commercial products to fulfil the requirements with regard to storage stability.

By the term "adrenaline" as used herein is meant the compound having the chemical formula (−)-3,4-dihydroxy-[(methylamino)methyl]benzyl alcohol. Adrenaline is also referred to as epinephrine.

Adrenaline may be obtained in one of its pharmaceutical acceptable salts. The hydrochloride, sulphate, and bitartrate salts are known to be used in pharmaceutical compositions. In the present invention the preferred salt of adrenaline is bitartrate.

The concentration of adrenaline in the injectable compositions of the present invention lies in the range of 0.2-50 µg/ml, such as for example in the range of 0.5-10 µg/ml adrenaline, such as 0.2-4 µg/ml adrenaline, such as 0.5-4 µg/ml adrenaline, such as 1 to 3 µg/ml adrenaline, such as about 2 µg/ml adrenaline. In a particular preferred embodiment of the present invention the concentration of adrenaline is 2 µg/ml.

The concentration of citric acid in the injectable compositions of the present invention lies in the range of 0.1-100 mM, such as for example in the range of 1-50 mM. In a particular preferred embodiment of the present invention the concentration of citric acid is 2.4 mM.

The solution pH in the injectable compositions of the present invention lies in the range of 2.5-3.5, such as for example in the range of 2.7-3.3. In a particular preferred embodiment of the present invention the solution pH is 3.

In a particular preferred embodiment the injectable composition of the present invention comprises 2 µg/ml adrenalin and 2.4 mM citric acid and has a solution pH of 3.

The inventors of the present invention have found that the presence of the 0.5 mg/ml Na-metabisulfite shows a destructive and destabilizing effect at 40° C., whereas traces of Na-metabisulfite seem to show no effect at all. It is therefore believed that the presence of Na-metabisulfite can totally be avoided in embodiments where the solutions are stored at temperatures lower than 40° C., such as for example at a temperature of 25° C. or lower.

In some embodiments the concentration of Na-metabisulfite in the injectable compositions of the present invention is lower than 100 µg/ml, such as for example lower than 50 µg/ml or 10 µg/ml or 5 µg/ml or 1 µg/ml.

The inventors of the present invention have also found that the presence of about 9 mg/ml NaCl may have a negative influence on storage stability at 40° C., whereas traces of NaCl seem to have no effect on the stability. Accordingly, in some embodiments the concentration of NaCl in the injectable compositions of the present invention is lower than 100 µg/ml, such as for example lower than 50 µg/ml or 10 µg/ml or 5 µg/ml or 1 µg/ml NaCl.

Hence, injectable compositions of the present invention, which are prepared for storage at about 40° C., preferably comprises 2 µg/ml adrenalin, 2.4 mM citric acid, less than 100 µg/ml Na-metabisulfite, less than 100 µg/ml NaCl and has a solution pH of 3.

In an embodiment the composition does not comprise lidocaine (also known as xylocaine, or lignocaine). In yet an embodiment the composition does not comprise an amino acid. It follows that an embodiment of the present invention does not comprise lidocaine and an amino acid, and a further embodiment does not comprise lidocaine or an amino acid. Thus in an embodiment the composition of the present invention is an injectable composition prepared for storage at about 40° C., which preferably comprises 0.2-4 µg/ml adrenaline, such as 2 µg/ml adrenaline, citric acid and does not comprise lidocaine and/or an amino acid.

The compositions of the present invention may further comprise an antioxidant. By the term "antioxidant" as used herein is meant a material that will prevent oxidation of adrenaline. Examples of antioxidants include cysteine, thioglycerol, acetylcysteine and ascorbic acid. The skilled person will know that citric acid may also be referred to as an antioxidant. In a preferred embodiment the compositions also comprises ascorbic acid in addition to citric acid.

The compositions of the present invention may further comprise a chelating agent. By the term "chelating agent" as used herein is meant a compound that is capable of forming chelating complexes or inclusion complexes with adrenaline. Examples of chelating agents include EDTA and EGTA. The skilled person would know that citric acid may also be referred to as a chelating agent. In a preferred embodiment the compositions also comprises EDTA in addition to citric acid.

The compositions of the present invention are formulated as injectable formulations. By the term "injectable formulation" or "injectable composition" as used herein is meant a formulation or composition, which is to be administered by injection or infusion techniques. Hence, the compositions may be administered via a parenteral route. As used herein, the term "parenteral" includes routes that bypass the alimentary tract. Hence, the term parenteral as used herein includes subcutaneous injections, intravenous, intramuscular, intrasternal, intracavernous, intrathecal injection or infusion techniques. Preferably the compositions of the present invention are administered intravenously.

Preferably the compositions of the present invention are administered such that a systemic concentration of adrenaline is achieved. A systemic concentration of adrenaline is obtained e.g. by intravenous injection as sites that result in the composition spreading rapidly through the body. Furthermore, a systemic concentration may be obtained by injecting the composition intravenously at sites that do not immediately direct the composition to the liver. Thus in an embodiment the composition according to the present invention is administered by parenteral administration, such as intravenous injection, resulting in a systemic concentration of adrenaline.

The injectable pharmaceutical composition is preferably sterile. It may also be desirable to include other components in the preparation, such as delivery vehicles including but not limited to aluminum salts, water-in-oil emulsions, biodegradable oil vehicles, oil-in-water emulsions, biodegradable microcapsules, and liposomes.

In a preferred embodiment the compositions of the present invention is formulated as an injectable formulation for use as an intravenous solution. Such composition may further comprise excipients approved for use in intravenous solutions, such as glucose, glycerol and/or lactic acid.

The injectable pharmaceutical compositions of the present invention may be used in the treatment of an adrenaline-requiring condition in a mammal subject in need thereof, where the mammal subject is administered an effective therapeutic amount of the composition.

By the term "adrenaline-requiring condition" as used herein is meant any medical condition wherein administration of adrenaline to an individual having the condition has a pharmacologically beneficial effect, such as improving at least one symptom of the medical condition. In some embodiments the adrenaline-requiring condition is acute hypersensitivity, such as anaphylactic reaction, asthmatic condition or cardiac arrest. In other embodiments the adrenaline-requiring condition is a bleeding disorder. In particular, the adrenaline-requiring condition is selected from the group consisting of coagulation disorder, bleeding, excessive bleeding and bleeding caused by tissue damage or surgical procedure.

The mammal subjects to be treated are preferably human being. However, other subject, such as for example dog, cat, horse, cow, goat and sheep may also be treated by the composition of the present invention. In an embodiment the human being has normal hemodynamics, i.e. normal clot strength and stability.

Thus in an embodiment the invention relates to a method for treatment of and/or reduction of bleeding, comprising enteral or parenteral administration of a composition comprising adrenaline as disclosed herein to a human being resulting in a systemic concentration of said adrenaline.

Pharmaceutical compositions of the present invention comprise an effective amount of adrenaline. The adrenaline may be dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains adrenaline and citric acid and optionally other pharmaceutical acceptable excipients will be known to those of skill in the art in light of the present disclosure, as exemplified by Remington's Pharmaceutical Sciences, 18th Ed. Mack Printing Company, 1990, incorporated herein by reference.

The injectable pharmaceutical compositions show superior storage stability, especially at temperatures below 40° C. When stored at temperatures around 40° C. there seems to be an upper limit for the concentration of Na-metabisulfite and NaCl if a satisfactory storage period wishes to be obtained. Moreover, since the compositions are formulated as ready-to-use formulations, the compositions are particular suitable for storage in emergency places such as pharmacies, hospitals and/or homes, in mobile or emergency medical aid kits, for travelers (especially to remote areas), for medical facilities lacking reliable refrigerated storage or hygienic conditions for sterile reconstitution of an injectable drug, and other contexts where stable, long-term storage of a stable pharmaceutical solution at ambient temperature may offer convenience, safety and/or cost-savings. Thus it is an object of the present invention to provide a composition as disclosed in any of the above which has excellent storage stability.

EXAMPLES

List of reagents:

Adrenalin "SAD" available from Amgros I/S, Copenhagen, Denmark

Citric acid as monohydrate available from Sigma-Aldrich, St. Louis, USA

NaCl, PhEur quality available from Merck KGaA, Darmstadt, Germany

NaCl, Ultrapure available from Sigma-Aldrich St. Louis, Mo., USA

Na-metabisulfite available from Sigma-Aldrich, St. Louis, USA

Ascorbic acid available from Sigma-Aldrich, St. Louis, USA

EDTA available from Sigma-Aldrich, St. Louis, USA

Glucose available from Sigma-Aldrich, St. Louis, USA

Glycerol available from Sigma-Aldrich, St. Louis, USA

Lactic acid available from Sigma-Aldrich, St. Louis, USA

All samples contain traces from the Adrenalin SAD excipients: Na-metabisulfite 1 μg/ml and NaCl 17 μg/ml and MPO 2 μg/ml. In all samples Adrenalin SAD 1 mg/ml is diluted 500 times.

Container used for storage of the formulation solutions: Vial: Cronus Clear 12×32 mm 8 mm screw part no. VZS-0208C; Closure: Cronus part no. VCA-0804TB.

Analytical Test Methods:

In all samples the content of adrenalin were determined by test method no. 2611-300 "U-Adrenalinium". The tests were performed by Unilabs A/S, Copenhagen, Denmark.

The test conditions have been chosen in order to promote an accelerated degradation of adrenaline by subjecting the test samples to diffuse day light and temperatures as high as 40° C. In real life medicaments will always be stored in darkness and typically at low temperatures. Only in extreme situations, such as in warm countries, where no refrigeration is available, storage at high temperatures such as 40° C. will occur.

Moreover, the test conditions are not fully reproducible: The subjection of test samples to diffuse day light was achieved by placing the test samples at a controlled temperature, but placed unprotected against light in an incubator with transparent lid and facing against a window from where the samples were exposed to a seasonally and weather depend amount of diffuse day light. The samples were also exposed regularly to artificial ceiling lighting. With this set-up samples placed in the same position during the same period of time can be compared, whereas samples tested during different periods of time have not been stressed to the same degree of sunlight and therefore test results from these two sets of experiments should only very carefully be compared. However, the indications revealed in each test should be reliable and reproducible.

Below all samples of Example 1 were tested during the same period of time. The same goes for all test samples of Example 2, 3 and 4, respectively. Hence, test results within the same Example are comparable, whereas test results of one example are not directly comparable with test results of another example.

Example 1

Test of Antioxidant's and Chelator's Effect on Storage Stability

All test samples were prepared by adding adrenaline to a volumetric container to give a final concentration of 0.002 mg/ml. Next Ultrapure NaCl was added to give a final concentration of 8.5 mg/ml, and then optionally either ascorbic acid (final concentration of 0.5 mg/ml) and/or Na-metabisulfite (final concentration of 0.5 mg/ml) and/or EDTA (final concentration of 0.5 mg/ml) and/or citric acid (final concentration of 0.5 mg/ml) was added in order to obtain solutions having the chemical compositions as listed in Tables 1.1 to 1.4. The solution pH was adjusted to either pH=3 or pH=4 by use of diluted NaOH/HCl Then two samples of each solution were transferred to a container used for storage.

Each container was then stored for two weeks at two different conditions; At 40° C. in diffuse daylight (DDL) or at 5° C. protected against daylight. After end storage the concentration of adrenaline was measured and compared to the starting concentration of 12.5 micromole/l.

Results

The results are shown below in Tables 1.1-1.4.

TABLE 1.1

Stored for 2 weeks in diffuse daylight at 40° C. Solution pH = 3

| Chelator |  | EDTA | citrate |  | EDTA | citrate |  | EDTA | citrate |
|---|---|---|---|---|---|---|---|---|---|
| Antiox. | ascorb | ascorb | ascorb | bisulf | bisulf | bisulf |  |  |  |
| Conc | 11 | 12.5 | 9.9 | 1.6 | 0 | 1.1 | 12.5 | 10.4 | 12.4 |
| Rel. to 12.5 | 88% | 100% | 79% | 13% | 0% | 9% | 100% | 83% | 99% |

TABLE 1.2

Stored for 2 weeks in diffuse daylight at 40° C. Solution pH = 4

| Chelator |  | EDTA | citrate |  | EDTA | citrate |  | EDTA | citrate |
|---|---|---|---|---|---|---|---|---|---|
| Antiox. | ascorb | ascorb | ascorb | bisulf | bisulf | bisulf |  |  |  |
| Conc | 7.8 | 8.9 | 5.2 | 0.1 | 0 | 0.5 | 0 | 3.7 | 7.3 |
| Rel. to 12.5 | 62% | 71% | 42% | 1% | 0% | 4% | 0% | 30% | 58% |

TABLE 1.3

Stored for 2 weeks protected against daylight at 5° C. Solution pH = 3

| Chelator |  | EDTA | citrate |  | EDTA | citrate |  | EDTA | citrate |
|---|---|---|---|---|---|---|---|---|---|
| Antiox. | ascorb | ascorb | ascorb | bisulf | bisulf | bisulf |  |  |  |
| Conc | 11.7 | 12.5 | 11.9 | 11.9 | 11.8 | 11.9 | 12.3 | 12.2 | 12.5 |
| Rel. to 12.5 | 94% | 100% | 95% | 95% | 94% | 95% | 98% | 98% | 100% |

TABLE 1.4

Stored for 2 weeks protected against daylight at 5° C. Solution pH = 4

| Chelator |  | EDTA | citrate |  | EDTA | citrate |  | EDTA | citrate |
|---|---|---|---|---|---|---|---|---|---|
| Antiox. | ascorb | ascorb | ascorb | bisulf | bisulf | bisulf |  |  |  |
| Conc. | 10.8 | 10.7 | 11.5 | 11.3 | 11.4 | 10.5 | 0 | 12.3 | 12.4 |
| Rel. to 12.5 | 86% | 86% | 92% | 90% | 91% | 84% | 0% | 98% | 99% |

The results show that:

a low solution pH is beneficial for the stability of adrenaline solution and a solution pH of 3 seems to be the best, the presence of the antioxidant Na-metabisulfite shows a destructive and destabilizing effect at 40° C., ascorbic acid is a much better antioxidant than Na-metabisulfite, in general good results can be achieved even without antioxidants, especially if pH is close to 3, the chelator EDTA has a good stabilizing effect both alone and in combination with ascorbic acid, and citric acid without antioxidants has a good stabilizing effect.

Citric acid is not just a good chelator, but also a good buffer in this acidic pH range.

All in all it may be concluded that the data indicate that adrenaline 0.002 mg/ml at pH 3 can be stabilized with citric acid as the only stabilizer.

Example 2

Influence of NaCl Quality on the Storage Stability

All test samples were prepared by adding adrenaline to a volumetric container to give a final concentration of 0.002 mg/ml. Next citric acid monohydrate was added to give a final concentration of 0.5 mg/ml and optionally NaCl, PhEur quality (final concentration of 8.5 mg/ml) or NaCl, Ultrapure (final concentration of 8.5 mg/ml). The solution pH was adjusted to pH=3 by use of diluted NaOH/HCl.

Then twelve samples of each solution were transferred to a container used for storage.

Three containers of each combination was then stored at different conditions with regard to light (diffuse daylight (DDL) or dark) and temperature (−20° C., 5° C., 25° C. or 40° C.). After 1 or 3 months storage the appearance of the samples were registered and the concentration of adrenaline was measured and compared to the starting concentration of 11.5 micromole/l.

Results

The results are shown below in Tables 2.1 and 2.2.

TABLE 2.1

Stability matrix - after 1 months

| Light | DDL | DDL | DDL | Dark | Dark | Dark |
|---|---|---|---|---|---|---|
| Temp | 40° C. | 40° C. | 40° C. | 5° C. | 5° C. | 5° C. |
| NaCl | PhEur | Ultra | None | PhEur | Ultra | None |
| Conc | 5.21 | 5.65 | 10.9 | 11.7 | 11.4 | 11.6 |
| Rel to 11.5 | 45% | 49% | 95% | 102% | 99% | 101% |
| appearance | C&C | C&C | C&C | C&C | C&C | C&C |
| Light | DDL | DDL | DDL | Dark | Dark | Dark |
| Temp | 25° C. | 25° C. | 25° C. | −20° C. | −20° C. | −20° C. |
| NaCl | PhEur | Ultra | None | PhEur | Ultra | None |
| Conc | 11.2 | 11.6 | 11.3 | 11.5 | 11.4 | Not tested |
| Rel to 11.5 | 97% | 101% | 98% | 100% | 99% | |
| appearance | C&C | C&C | C&C | C&C | C&C | Fractured |

C&C: clear & colorless solution;
Fracture: all vials fractured due to icing

TABLE 2.2

Stability matrix - after 3 months

| Light | DDL | DDL | DDL | Dark | Dark | Dark |
|---|---|---|---|---|---|---|
| Temp | 40° C. | 40° C. | 40° C. | 5° C. | 5° C. | 5° C. |
| NaCl | PhEur | Ultra | None | PhEur | Ultra | None |

TABLE 2.2-continued

Stability matrix - after 3 months

| Conc | 0.1 | 0.27 | 8.6 | 11.1 | 11.4 | 11.3 |
|---|---|---|---|---|---|---|
| Rel to 11.5 | 1% | 2% | 75% | 97% | 99% | 98% |
| appearance | C&C | C&C | C&C | C&C | C&C | C&C |
| Light | DDL | DDL | DDL | Dark | Dark | Dark |
| Temp | 25° C. | 25° C. | 25° C. | −20° C. | −20° C. | −20° C. |
| NaCl | PhEur | Ultra | None | PhEur | Ultra | None |
| Conc | 7.86 | 9.04 | 11 | 11.1 | 11.1 | Not tested |
| Rel to 11.5 | 68% | 79% | 96% | 97% | 97% | |
| appearance | C&C | C&C | C&C | C&C | C&C | Fractured |

C&C: clear & colorless solution;
Fracture: all vials fractured due to icing

The results show that:

all samples stored protected against daylight at 5° C. are stable for more than 3 months, the stability of samples stored in diffuse daylight at 40° C. is strongly and negatively influenced by NaCl, and at 25° C. there seem to be a tendency of NaCl to negatively affect the stability; samples stored at 25° C. in darkness, where not tested, Ultrapure quality is better than the PhEur quality, but the best results are obtained with the NaCl-free samples, and the stability of NaCl-containing samples at −20° C. in darkness are stable for more than 3 months, whereas the cartridges of all NaCl-free samples are fractured during storage due to icing.

Example 3

Influence of Liquid Tonicity on the Storage Stability—3 Months Storage

All test samples were prepared by adding adrenaline to a volumetric container to give a final concentration of 0.002 mg/ml. Next citric acid was added to give a final concentration of 0.5 mg/ml and then optionally a tonicity agent of either glucose (final concentration of 50 mg/ml), glycerol (final concentration of 25 mg/ml), lactic acid (final concentration of 16 mg/ml) or NaCl (final concentration of 9 mg/ml). The solution pH was adjusted to pH=3 by use of diluted NaOH/HCl.

Then 6 samples of each solution were transferred to the containers used for storage.

The samples were stored for 3 months at different storage conditions with regard to light (diffuse daylight (DDL) or dark) and temperature (−20° C., 5° C., 25° C. or 40° C.). After end storage the concentration of adrenaline was measured and compared to the equivalent sample stored at 5° C.

Results
The results are shown below in Table 3.1

TABLE 3.1

Stability matrix - after 3 months

| tonicity | glucose | glycerol | lactic | NaCl | none | glucose | glycerol | lactic | NaCl | none |
|---|---|---|---|---|---|---|---|---|---|---|
| Light | DDL | DDL | DDL | DDL | DDL | dark | dark | dark | dark | dark |
| temp | 40° C. | 40° C. | 40° C. | 40° C. | 40° C. | 40° C. | 40° C. | 40° C. | 40° C. | 40° C. |
| Conc | 8.8 | 8.8 | 8.5 | 2.7 | 9.9 | 9.7 | 9.1 | 10 | 3.1 | 9.9 |
| Rel to 5° C. | 82% | 83% | 82% | 25% | 93% | 91% | 86% | 96% | 29% | 93% |
| Light | DDL | DDL | DDL | DDL | DDL | dark | dark | dark | dark | dark |
| temp | 25° C. | 25° C. | 25° C. | 25° C. | 25° C. | 25° C. | 25° C. | 25° C. | 25° C. | 25° C. |
| Conc | 11.5 | 10.6 | 10.4 | 10.9 | 10.7 | 10.5 | 10.5 | 10.5 | 10.6 | 10.9 |
| Rel to 5° C. | 107% | 100% | 100% | 102% | 100% | 98% | 99% | 101% | 99% | 102% |
| Light | Dark | dark | dark | dark | dark | dark | dark | dark | dark | dark |
| temp | 5° C. | 5° C. | 5° C. | 5° C. | 5° C. | −20° C. | −20° C. | −20° C. | −20° C. | −20° C. |
| Conc | 10.7 | 10.6 | 10.4 | 10.7 | 10.7 | | | | | |
| Rel to 5° C. | 100% | 100% | 100% | 100% | 100% | | | | | |

DDL: Diffuse daylight;
dark: protected against daylight
Note:
samples >100%: probably due to evaporation from the container.

The results of this experiments show the following indications:

Storage conditions: Diffuse daylight versus Protected against day light (dark): After 3 months the results show a significant difference between storage at diffuse daylight and dark conditions at 40° C., where storage at dark conditions show the best result as expected, Stability after 3 months at 40° C.: The negative influence of isotonic NaCl in adrenaline solutions has been confirmed. The best result is obtained in formulations free of tonicity adjusting agent (i.e. the samples designated: none), The three alternative candidates glucose, glycerol and lactic acid are very similar when stored at diffuse daylight and much better candidates than NaCl, and Stability after 3 months at 25° C.: All samples are stable (>95%) after 3 months at 25° C.

Example 4

Influence of Liquid Tonicity on the Storage Stability—6 Months Storage

A continuation of Example 3: The samples have been stored for 6 months instead of 3 months.

Results
The results are shown below in Table 4.1

TABLE 4.1

Stability matrix - after 6 months

| tonicity | glucose | glycerol | lactic | NaCl | none | glucose | glycerol | lactic | NaCl | none |
|---|---|---|---|---|---|---|---|---|---|---|
| Light | DDL | DDL | DDL | DDL | DDL | dark | dark | dark | dark | dark |
| temp | 40° C. | 40° C. | 40° C. | 40° C. | 40° C. | 40° C. | 40° C. | 40° C. | 40° C. | 40° C. |
| Conc | 7.4 | 6.8 | 5.4 | 0.2 | 6.7 | 7.2 | 7.5 | 7.6 | 0.2 | 8.1 |
| Rel to 5° C. | 69% | 62% | 51% | 2% | 59% | 67% | 69% | 72% | 2% | 72% |
| Light | DDL | DDL | DDL | DDL | DDL | dark | dark | dark | dark | dark |
| temp | 25° C. | 25° C. | 25° C. | 25° C. | 25° C. | 25° C. | 25° C. | 25° C. | 25° C. | 25° C. |
| Conc | 10.5 | 10.6 | 9.7 | 10.7 | 11.2 | 10.5 | 10.4 | 10.0 | 10.4 | 11.2 |
| Rel to 5° C. | 97% | 97% | 92% | 103% | 99% | 97% | 95% | 94% | 100% | 99% |
| Light | Dark | dark | dark | dark | dark | dark | dark | dark | dark | dark |
| temp | 5° C. | 5° C. | 5° C. | 5° C. | 5° C. | −20° C. | −20° C. | −20° C. | −20° C. | −20° C. |
| Conc | 10.8 | 10.9 | 10.6 | 10.4 | 11.3 | 10.9 | 11.2 | 10.7 | 11.3 | 11.1 |
| Rel to 5° C. | 100% | 100% | 100% | 100% | 100% | 100% | 100% | 100% | 100% | 100% |

DDL: Diffuse daylight;
dark: protected against daylight
Note:
samples >100%: probably due to evaporation from the container.

The results of this experiments show the following indications:

Storage conditions: After 6 months, a significant difference between storage at diffuse daylight and dark conditions at 40° C. can be detected, Stability after 6 months at 40° C.: The negative effect of isotonic NaCl at 40° C. has been confirmed, and it is indicated that the alternative candidates glucose, glycerol and lactic acid are rather similar and much more promising candidates; at 25° C. the stability of samples comprising NaCl seems to be satisfactory, Stability after 6 months at 25° C., 5° C. and −20° C.: All samples seem to be stable after 6 months storage at 25° C., 5° C. and −20° C.

The invention claimed is:

1. An injectable pharmaceutical composition comprising:
   I: (a) 0.2-50 μg/ml adrenaline, and
   (b) citric acid, and
   (c) no lidocaine and no amino acid.

2. The composition according to claim 1, wherein the concentration of adrenaline lies in the range of 0.5-10 μg/ml adrenaline.

3. The composition according to claim 1, wherein the concentration of citric acid lies in the range of 0.1-100 mM.

4. The composition according to claim 1, wherein the solution pH lies in the range of 2.5-3.5.

5. The composition according to claim 1 comprising 2 µg/ml adrenaline, 2.4 mM citric acid and where the solution pH is 3.

6. The composition according to claim 1, wherein the composition further comprises Na-metabisulfite and where the concentration of Na-metabisulfite is no more than 100 µg/ml.

7. The composition according to claim 1, wherein the composition further comprises NaCl and where the concentration of NaCl is no more than 100 µg/ml.

8. The composition according to claim 1 further comprising an antioxidant.

9. The composition according to claim 1 further comprising a chelating agent.

10. The composition according to claim 1, wherein the composition is formulated as an injectable solution.

11. The composition according to claim 1 further comprising an excipient approved for use in formulation for use as intravenous solutions.

12. The composition according to claim 1 which has storage stability of greater than 95% stable at 3 months at 25 degrees Celsius.

13. A method of treating an adrenaline-requiring condition in a mammalian subject in need thereof, said method comprising administering an effective therapeutic amount of the composition according to claim 1 to the mammalian subject.

14. The method according to claim 13, wherein the adrenaline-requiring condition is selected from the group consisting of coagulation disorder, bleeding, and bleeding caused by tissue damage or surgical procedure.

15. The method according to claim 13, wherein the mammalian subject is a human.

16. The method according to claim 13, wherein the composition is administered parenterally resulting in a systemic concentration of adrenaline.

17. The method according to claim 13, wherein the composition comprises 0.2-50 µg/ml adrenaline and 0.1 to 100 mM citric acid, said composition having a pH in the range of 2.5-3.5.

* * * * *